United States Patent [19]

Wicks, III et al.

[11] Patent Number: 4,736,627
[45] Date of Patent: Apr. 12, 1988

[54] STEAM PROFILE LIQUID/VAPOR SEPARATOR

[75] Inventors: Moye Wicks, III; Boyd B. Moore, both of Houston, Tex.

[73] Assignee: Shell Oil Company, Houston, Tex.

[21] Appl. No.: 813,289

[22] Filed: Dec. 24, 1985

Related U.S. Application Data

[63] Continuation-in-part of Ser. No. 671,657, Nov. 15, 1984, Pat. No. 4,581,926.

[51] Int. Cl.⁴ .............................................. E21B 47/00
[52] U.S. Cl. ...................................... 73/155; 55/462; 166/303
[58] Field of Search ............... 73/155, 29, 30; 55/443, 55/462, 463; 166/250, 252, 264, 272, 303; 374/42

[56] References Cited

U.S. PATENT DOCUMENTS

| 680,717 | 8/1901 | Labadie | 55/463 |
| 1,311,573 | 7/1919 | Newburgh | 55/463 |
| 2,654,433 | 10/1953 | Piety | 73/155 |
| 3,413,838 | 12/1968 | Duddy | 73/29 |
| 3,934,469 | 1/1976 | Howard et al. | 73/155 |
| 4,088,187 | 5/1978 | Howard et al. | 73/155 X |
| 4,409,825 | 10/1983 | Martin et al. | 73/155 |
| 4,547,078 | 10/1985 | Long et al. | 374/42 |
| 4,581,926 | 4/1986 | Moore et al. | 73/155 |

FOREIGN PATENT DOCUMENTS

| 1078045 | 3/1984 | U.S.S.R. | 73/155 |
| 1078044 | 3/1984 | U.S.S.R. | 73/155 |

Primary Examiner—Stewart J. Levy
Assistant Examiner—Kevin D. O'Shea

[57] ABSTRACT

A network of bristles extending across a steam injection well provides affirmative liquid/vapor separation and control. The orientation of the bristles is controlled to direct the liquid toward or away from the borehole wall as desired.

29 Claims, 2 Drawing Sheets

STEAM PROFILE LIQUID/VAPOR SEPARATOR

CROSS-REFERENCE TO RELATED APPLICATION

The present application is a continuation-in-part of U.S. application Ser. No. 671,657 (Moore, et al, filed Nov. 15, 1984), assigned to the assignee of the present invention, and now U.S. Pat. No. 4,581,926 issued Apr. 15, 1986.

BACKGROUND OF THE INVENTION

The present invention relates to the production of liquid hydrocarbons, and more particularly to the production of liquid hydrocarbons using various thermal methods.

The enhanced recovery of oil, and particularly heavy crude deposits, has increased during recent years as a result of decreasing reserves and increasing prices. These factors have increasingly made thermal recovery methods more and more economically attractive.

In thermal recovery processes using steam, two methods are primarily used. In the first, steam is injected into the formation for a period of time, after which the well is shut in and allowed to soak. Following the soaking period, the crude oil that accumulates in the well is produced, and the process is repeated. In the second method, the steam is used not only to heat the formation, but also to drive the crude toward a producing well. In both of these methods, the steam flows through perforations in the casing in the injection well, and it is thus highly desirable to know the injection profile of the steam entering the formation. That is, a steam injection/thermal recovery program is based upon a predetermined pattern (usually uniform) of steam entry into the formation. It is accordingly important to know whether or not the steam is entering as desired, and not bypassing one or more portions of the formation. It is also desirable to know the quality (liquid/vapor ratio) of the steam being injected into each portion of the formation, since this tremendously affects the amount of heat actually being transported into the formation and into the crude oil deposits therein.

In U.S. Pat. No. 4,581,926 (U.S. application Ser. No. 671,657, filed Nov. 15, 1984), mentioned above, a substantially improved method and apparatus are disclosed for downhole measurements of the quantity and quality of steam being injected into a well. When used with multiple perforation zones, that invention provides a direct means for determining the amount of thermal energy flowing into each zone. The invention thus represents a substantial improvement over prior art methods and apparatus. However, typical injection regimes involve multi-phase flow. That is, a mixture of steam (vapor) and steam condensate (liquid) at temperature-pressure equilibrium is flowing through the well toward and into the formation. This gas-liquid flow stream presents unique challenges from the standpoint of the actual phase distribution therein. That is, at any given location, particularly in wells which may be even slightly deviated, it is oftentimes not safe to infer homogeneity of the phases. Rather, it is entirely possible that the bulk of the liquid may be cascading down the wall of the well along one (usually the lower) side thereof.

In such a case, two problems become immediately apparent. First, a method and apparatus such as disclosed in the above-noted '926 patent ('657 application), which implicitly assumes a fairly homogeneous phase flow, may produce a consequent error. That is, because it intercepts a fractional part of the flow which is taken to fairly represent the whole, then to the extent that the flow is inhomogeneous, the amounts of each phase which are reported in toto may be affected accordingly. Secondly, a heavy wash of liquid across the perforations through which the steam is being injected will result in a much higher proportion of liquid being injected than would be anticipated assuming homogeneity of the phases. Since the heat content of the liquid phase is far less than the vapor phase, the heat injection profile which is calculated will be skewed to that extent.

A need therefore remains for an improved method and apparatus for measuring the steam liquid/vapor profile, particularly where that profile at any given point in the well may not be homogeneous.

SUMMARY OF THE INVENTION

Briefly, the present invention meets the above needs and purposes with a new and improved method and apparatus for separating the liquid and vapor phases for determining steam quality in a thermal injection well. By this means, the steam liquid/vapor profile can be determined accurately even though the flow of the phases may not be homogeneous at the region in which the measurement is made. With the present invention, therefore, measurements can be made above and below a perforation zone and an accurate determination made of the actual amount of thermal energy flowing into that zone.

According to the present invention, a series of wire bristles temporarily separates the vapor and the liquid condensate. The bristles are preferably wire filaments having a spring action and being wettable by the liquid phase of the steam. More particularly, the preferred embodiment of the invention includes a housing which is moveable longitudinally within the well and contains an appropriate measuring device for measuring the liquid/vapor profile of a portion of the fluid flowing therethrough. The housing supports a plurality of the bristles near the upper portion of the housing.

In the preferred embodiment, the bristles very much resemble a wire brush. That is, they are attached in a basically uniform pattern of many vertically spaced horizontal rows, each row radiating outwardly from a central core. The bristles all have a length greater than the radius of the borehole, and are thus curved or bent against the sides of the borehole. In the preferred embodiment, the ends of the bristles thus come into substantially tangential contact with the borehole wall, and tend to "capture" the liquid droplets which come in contact therewith and guide them in the downstream direction of the bristles. That is, the liquid which contacts the bristles tends to migrate along the bristles in the direction thereof most nearly parallel to the net flow direction of the vapor in the well.

A large number of bristles is used, thus forming a network extending across substantially the entire cross-sectional area of the well at the location of the bristles. The bristles accordingly form a tortuous path for the liquid and vapor flowing downwardly therepast, for effectively intercepting the liquid portion of the fluid flow. Since the bristles are angled with respect to the longitudinal and radial directions of the borehole (due to their being longer than the radius of the borehole), they will point either in a generally downward or a generally upward direction. When pointed in a downward direction toward the wall of the well, the bristles will tend to direct the liquid in the flow toward the walls of the well, since the steam vapor is flowing downwardly in the injection process. Conversely, when pointed upwardly (i.e., angled radially inwardly in a downward direction substantially toward the center of the well), the bristles will direct liquid which comes in contact with them inwardly toward the center of the well. In the preferred embodiment, the measuring device is located in the tool housing at the center of the well. Accordingly, the bristles can direct substantially the entire liquid flow either away from the measuring portion of the tool or directly to it. Therefore, the liquid phase and the vapor phase of the steam can be individually and accurately measured at any desired point in the well.

Ideally, the direction in which the bristles "point", and thus the direction (radially inwardly or radially outwardly) in which the liquid phase is moved can be adjusted when the tool is down in the well. This is one reason that flexible bristles having a spring action are preferred in this invention. Thus, when the tool is first inserted into the well, the bristles will trail behind the tool housing, thus pointing upwardly, so that the liquid is directed toward the measuring means in the center of the tool. To reverse the bristles, the tool is simply lowered to a location below that where the measurement is to be made, and then pulled back up to that location. When the direction of the tool housing is reversed, the bristles, due to their tangential engagement with the borehole wall, will drag frictionally therealong, reverse, and again trail along "behind" the housing. Accordingly, the bristles are reversed and point in a downwardly outward direction. The liquid phase will then be conducted outwardly to the walls of the borehole. Lowering the tool will again reverse the bristles, and so forth. In those embodiments where particularly stiff bristles may be used, according to the preferences of the particular tool operator, it may be preferable to provide zones of larger diameter, or to move the tool into such pre-existing zones, to facilitate reversal of the bristles.

It is therefore an object of the present invention to provide a liquid-vapor separator and method therefor for downhole use with a steam thermal recovery process; such a method and apparatus wherein steam is being injected downwardly through a well into a hydrocarbon bearing formation surrounding the well; in which the liquid and vapor are separated by a plurality of bristles disposed within the well; in which the bristles are supported within the well at an angle with respect to the longitudinal and radial directions of the well; in which the bristles thus are supported in a network extending across substantially the entire cross-sectional area of the well at the location of the bristles, in which the bristles thus form a tortuous path for liquid and vapor flowing downwardly therepast., in which this configuration thus causes the bristles to direct liquid which consequently contacts the bristles to migrate along the bristles in the direction thereof most nearly parallel to the net flow direction of the vapor in the well., in which the bristles are supportable on a housing moveable longitudinally within the well; in which such a housing also incorporates a measurement means for intercepting at least a portion of the steam and fluid flowing past the housing in the well and measuring the liquid/vapor profile thereof., and to accomplish the above objects and purposes in an inexpensive, uncomplicated, durable, versatile and reliable method and apparatus, inexpensive to manufacture and implement, and readily suited to the widest possible utilization in steam profile liquid/vapor measurements in thermal injection wells.

DESCRIPTION OF THE PREFERRED EMBODIMENT

Figure 1:
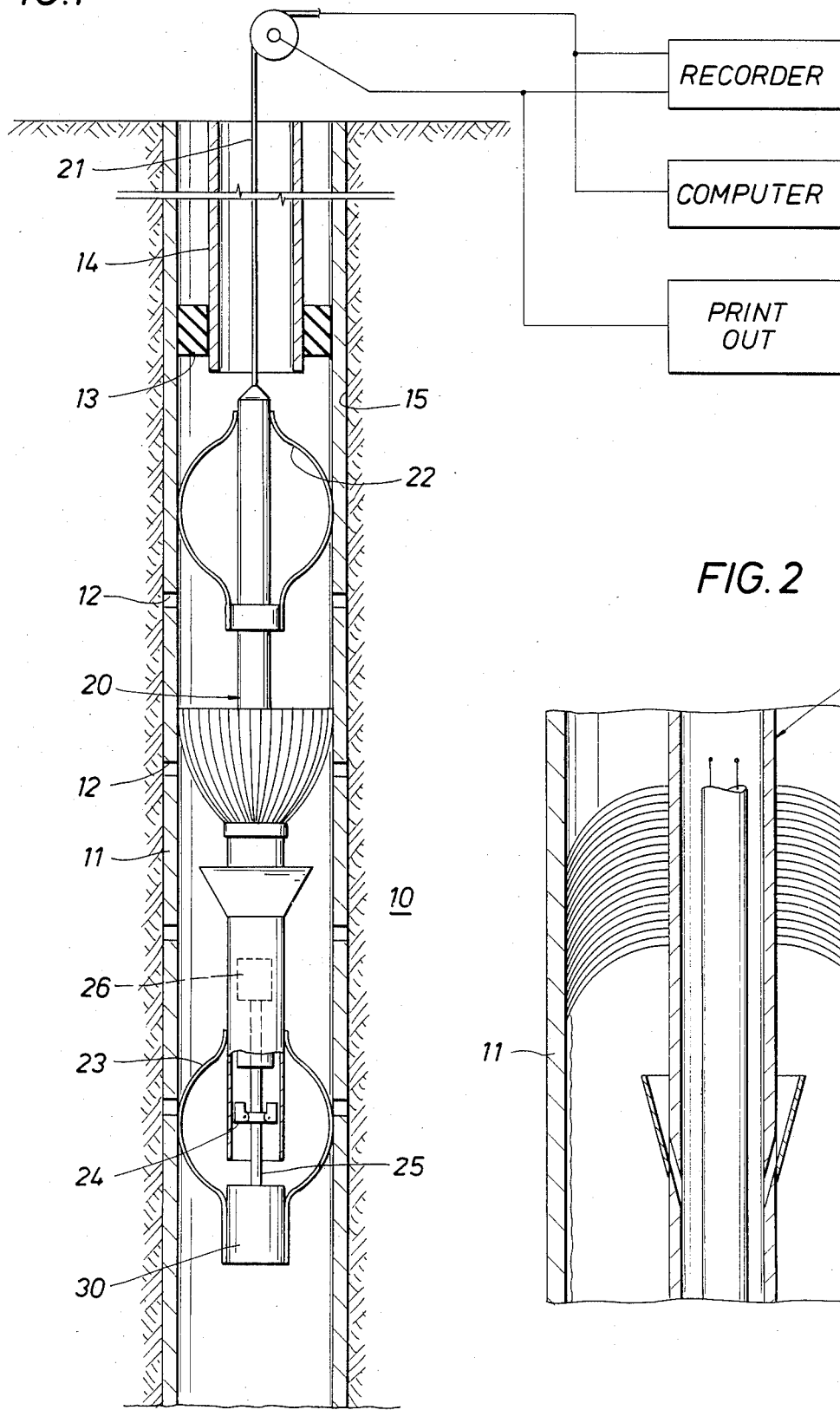
FIG. 1 is a figurative cross-sectional view of a steam injection well showing therein a steam quality measurement tool incorporating a liquid/vapor separator according to the present invention.

With reference to the drawings, the new and improved liquid/vapor separator for downhole use with a steam thermal recovery process, and the method therefor according to the present invention, will be described. FIG. 1 shows a formation 10 having a borehole 15 extending therethrough. As illustrated here, the borehole 15 is a cased borehole, lined by casing 11. A series of perforations 12 through casing 11 provides for injecting steam into the formation 10. The steam is transported from the surface to the formation by a tubing string 14 which extends into the cased hole. A packer 13 isolates the perforated part of the casing from the remainder of the casing.

The measurement apparatus includes a downhole sonde having a housing 20 which is lowered into the borehole through the tubing string 14 on a flexible conduit 21. The conduit 21, in addition to having the strength to support the sonde and raise and lower it in the borehole, also includes the electrical conductors required to transmit power and measurement signals to and from the housing 20. Typically, conduit 21 will be a high temperature armored cable. In the preferred embodiment, centralizers such as bow springs 22 and 23 assist in centering the tool housing 20 in the casing.

A measuring means, as more particulary described in the above-noted U.S. Pat. No. 4,581,926 (U.S. Ser. No. 671,657, filed Nov. 15, 1984), the description of which is incorporated herein by reference, is supported in housing 20, and includes a turbine wheel 24 mounted on the shaft 25 of a motor-generator 26. The lower end of the motor shaft 25 is supported by a pivot bearing carried in the bottom member 30 of the housing 20.

Figure 2:
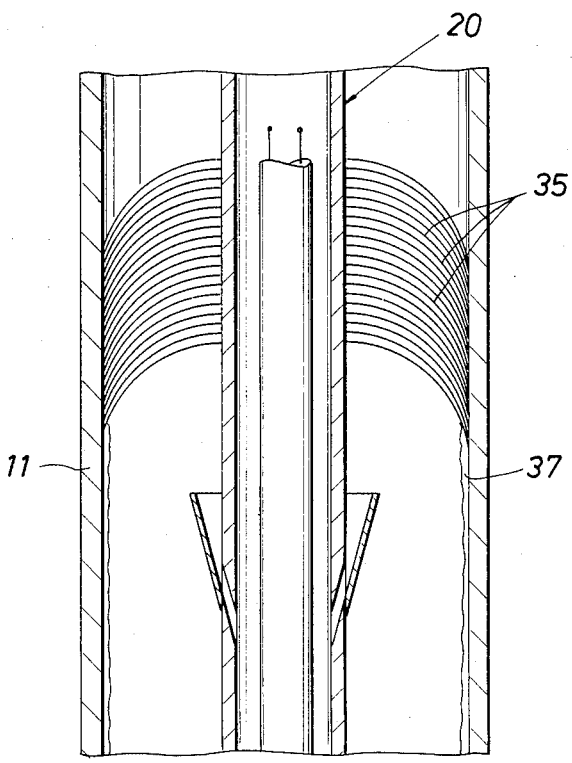
FIG. 2 is a fragmentary figurative illustration showing the bristles pointing downwardly to move liquid to the wall of the borehole.
Figure 3:
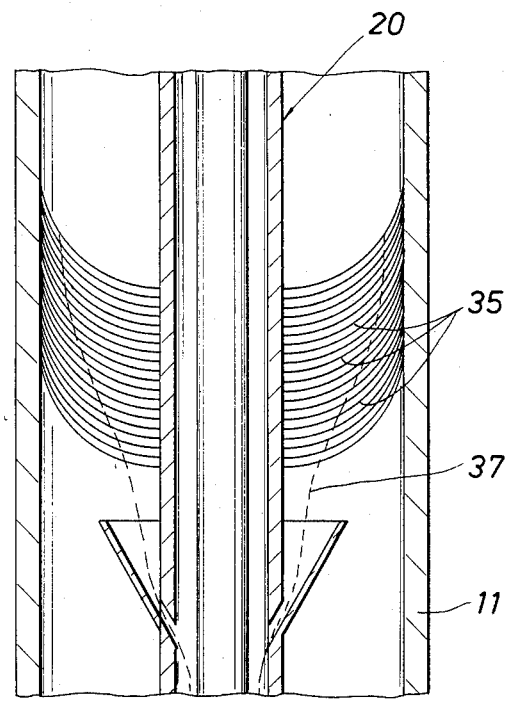
FIG. 3 is a fragmentary figurative illustration showing the bristles pointing upwardly to move liquid to the wall of the borehole.

In order to separate the liquid and vapor phases of the steam which is being injected, the present invention includes a plurality of bristles 35 radiating from and attached to the housing 20. In the preferred embodiment, the bristles have a length approximately 1.6 times the radius of the borehole, so that they are forced into a curved configuration, such as shown in FIGS. 1–3. The ends of the bristles, in the preferred embodiment, then touch the wall of casing 11 tangentially. When they point outwardly upwardly, as in FIG. 3, they accordingly conduct the liquid into the center of the borehole, and into housing 20 for measurement by turbine wheel 24 at the bottom thereof. Conversely, when the bristles point downwardly outwardly (FIG. 2), the liquid phase is directed away from housing 20 to the casing wall 11, so that only the vapor phase is measured by the turbine wheel 24. Accordingly, a very representative measurement of the liquid phase and an equally representative measurement of the vapor phase can each be independently made even though the overall flow just above the sonde may be very inhomogeneous.

Figure 4A:
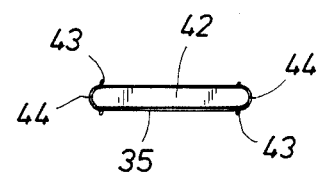
FIG. 4A is an end view of the fabrication structure illustrated in FIG. 4.
Figure 4:
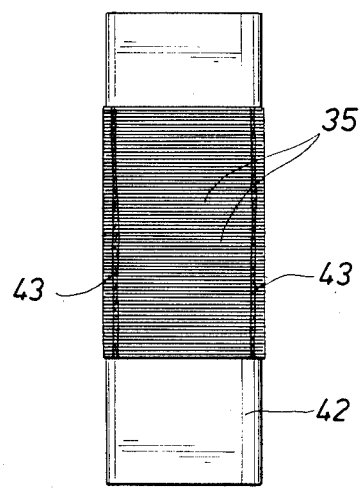
FIG. 4 illustrates fabrication of the brush.
Figure 5:
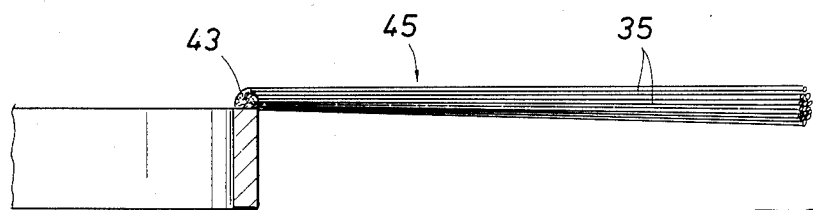
FIG. 5 is a fragmentary, cross-sectional view showing the brush mounted on the tool housing.
Figure 6:
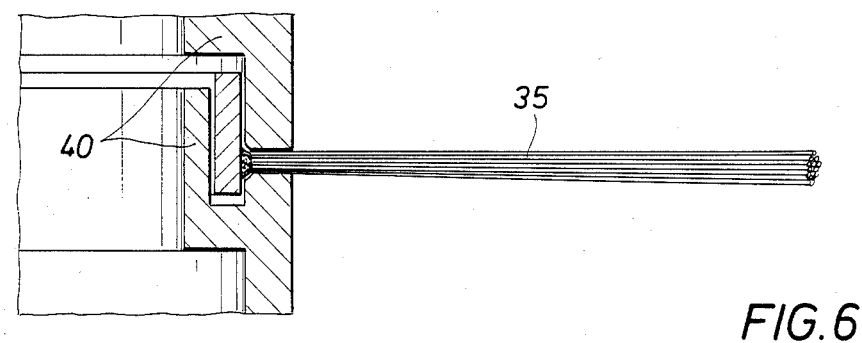
FIG. 6 shows an alternate means for securing and supporting the bristles.

In the preferred embodiment, the bristles 35 are arranged in many rows in series (FIGS. 1–3). This forms a network extending substantially across the entire cross-sectional area of the well at the location of the bristles. The tortuous path for the liquid and vapor flowing downwardly therepast accordingly causes the liquid 37 to contact the bristles and then migrate along the bristles in the downward direction thereof. When the bristles point downwardly outwardly (FIG. 2), the bristles cause the liquid to flow outwardly to the casing wall, as described, and vice versa. In the preferred embodiment, the bristles consist of 60–80 rows of 0.021 inch diameter stainless steel braided (7 strands) wire extending from the tool body. A suitable wire is multi-stranded wire manufactured to control the flight of model airplanes, having a size of 0.21". The wires may be attached in any suitable fashion to the housing 20. In the preferred embodiment, they are attached by mechanically clamping them such as in clamping devices 40 (FIG. 6). They can also be wrapped on a mandrel 42 (FIG. 4), welded together at bead 43, and cut at 44, to form brush rows 45 (FIG. 5). Clamping is presently preferred to avoid deleterious heat effects on the mechanical properties of the wire, such as yield strength, which would be reduced as a result of welding.

The bristle structure thus described can withstand the steam temperatures and the erosive effects of the liquid flow. The bristles also have sufficiently small cross-sectional areas that they provide tolerable pressure drops in the steam flow as it moves past them in the tubing. They also exhibit sufficient spring action to permit them to be inverted as desired within the borehole. Additionally, they are water-wettable, and readily suited for manufacture by mass-production methods.

Laboratory tests have shown the present invention to be highly effective liquid/vapor separation, such as for steam quality measurement. When bristles according to the present invention were placed in a test section oriented with their outward tips pointing upwardly, the bristles were very effective in diverting water from the wall region into the center of the casing. When inverted, the bristles were equally effective at diverting virtually all of the liquid outwardly to the wall of the casing.

It will also be seen that the present invention can be used not only for affirmatively controlling the liquid flow in a particular zone of a borehole for purposes of steam quality measurement, but for other purposes as well. For example, if too much liquid is being injected into a particular zone, bristles according to the present invention can be used just above the associated perforations to direct the liquid into the center of the borehole and thus past those perforations. Then the injected steam will be essentially liquid free in that zone. Conversely, the bristles could be used to increase the amount of liquid being injected by diverting the liquid to the casing wall so that the liquid washes across the perforations for increased injection thereof. A suitable bristle structure without the measuring apparatus (turbine 24, etc.) could be left permanently in place in the borehole to provide such control on a continuous basis.

As may be seen, therefore, the present invention has numerous advantages. As already discussed above, the ability to remove water film from the wall of the borehole is clearly necessary to make an accurate measurement of steam quality. Otherwise, the measurement will probably be inaccurate to the extent that the fluid flow is inhomogeneous. Therefore, whether attempting to homogenize the flow field, or trying to separate it into the liquid and vapor phases for measuring each phase alone, it is necessary to capture and control the water flow. The present invention accomplishes this object using bristles which intercept not only the fluid flow within the borehole, but which also contact the borehole wall itself, thereby providing a large number of contact points to which the water flowing therealong can attach. Having many rows of bristles in series, according to the invention, then provides multiple opportunities so that water escaping one line of bristles can readily be captured by the next, and so forth. The present invention thus provides a highly effective, inexpensive, uncomplicated, versatile, durable and reliable method and apparatus for liquid/vapor steam profile measurements of high accuracy, suitable for the widest possible utilization in steam injection wells and analogous applications.

While the methods and forms of the apparatus herein described constitute preferred embodiments of this invention, it is to be understood that the invention is not limited to these precise methods and forms of apparatus, and that changes may be made therein without departing from the scope of the invention.

What is claimed is:

1. A liquid/vapor separator for downhole use with a steam thermal recovery process wherein steam is being injected downwardly through a well into a hydrocarbon bearing formation surrounding the well, comprising:
(a) a plurality of bristles having a length approximately 1.6 times greater than the radius of the well, disposed within the well, and formed of a wire filament material having a spring action and being wettable by the liquid flowing therepast, and
(b) bristle supporting means supporting a series of rows of said bristles in a predetermined pattern within the well at angles with respect to the longitudinal and radial directions of the well to hold said bristles in a network extending across substantially the entire cross-sectional area of the well at the location of said bristles, to form a tortuous path for liquid and vapor flowing downwardly therepast, and to cause said bristles to direct liquid which consequently contacts said bristles to migrate along said bristles in the direction thereof most nearly like the net flow direction of the vapor in the well, said bristle supporting means including:
(i) means supporting said bristles for changing said angles thereof with respect to the longitudinal and radial directions of the well to change the radial component of said direction in which said bristles cause the liquid which contacts said bristles to flow and to cause said bristles to direct liquid in contact therewith along said bristles accordingly, such that:

(a) when said bristle supporting means supports said bristles angled radially outwardly in a downward direction toward the wall of the well said bristles will direct the liquid which comes in contact with said bristles outwardly toward the wall of the well, and (b) when said bristle supporting means supports said bristles angled radially inwardly in a downward direction substantially toward the center of the well said bristles will direct the liquid which comes in contact with said bristles inwardly toward the center of the well, (ii) a central core around which said bristles are attached in a predetermined pattern radiating substantially uniformly outwardly around said central core and curved to a position substantially tangent to and touching the wall of the well, and (iii) clamp means for clamping said bristles to said central core.

2. Apparatus for downhole use with a steam thermal recovery process for determining the quality of steam being injected downwardly through a well into a hydrocarbon bearing formation surrounding the well, comprising:

(a) a housing movable longitudinally within the well, (b) measurement means supported on said housing for intercepting at least a portion of the steam fluid flowing past said housing in the well and measuring the liquid/vapor profile thereof, (c) a plurality of bristles, and (d) bristle supporting means supporting said bristles on said housing within the well at angles with respect to the longitudinal and radial directions of the well to hold said bristles in a network extending across substantially the entire cross-sectional area of the well at the location of said bristles, to form a tortuous path for liquid and vapor flowing downwardly therepast, and to cause said bristles to direct liquid which consequently contacts said bristles to migrate along said bristles in the direction thereof most nearly like the net flow direction of the vapor in the well.

3. The apparatus of claim 2 further comprising centralizer means attached to said housing for centering said housing in the well.

4. The apparatus of claim 2 wherein said bristle supporting means supports said bristles angled radially outwardly in a downward direction toward the wall of the well to direct the liquid which comes in contact with said bristles outwardly toward the wall of the well.

5. The apparatus of claim 2 wherein said bristle supporting means supports said bristles angled radially inwardly in a downward direction substantially toward the center of the well to direct the liquid which comes in contact with said bristles inwardly toward the center of the well.

6. The apparatus of claim 2 wherein said bristles comprise bristles formed of a material wettable by the liquid flowing therepast.

7. The apparatus of claim 6 wherein said bristles further comprise wire filaments.

8. The apparatus of claim 2 wherein said bristle supporting means further comprises a central core around which said bristles are attached in a predetermined pattern radiating outwardly therefrom.

9. The apparatus of claim 8 wherein said bristle supporting means further comprises clamp means for clamping said bristles to said central core.

10. The apparatus of claim 8 wherein said bristle supporting means further comprises means supporting said bristles in a predetermined pattern in which said bristles radiate radially outwardly from said central core substantially uniformly therearound.

11. The apparatus of claim 8 wherein said bristle supporting means further comprises means supporting said bristles in the well such that substantially each said bristle is curved to a position substantially tangent to and touching the wall of the well.

12. The apparatus of claim 11 wherein substantially all of said bristles each have a length greater than the radius of the well.

13. The apparatus of claim 2 wherein said bristle supporting means supports said bristles for changing said angles thereof with respect to the longitudinal and radial directions of the well to change the radial component of said direction in which said bristles cause the liquid which contacts said bristles to flow to cause said bristles to direct liquid in contact therewith along said bristles in the opposite radial direction.

14. Apparatus for downhole use with a steam thermal recovery process for determining the quality of steam being injected downwardly through a well into a hydrocarbon bearing formation surrounding the well, comprising:

(a) a housing movable longitudinally within the well, (b) measurement means supported on said housing for intercepting at least a portion of the steam fluid flowing past said housing in the well and measuring the liquid/vapor profile thereof, (c) a plurality of bristles having a length approximately 1.6 times greater than the radius of the well and formed of a wire filament material having a spring action and being wettable by the liquid flowing therepast, and (d) bristle supporting means supporting a series of rows of said bristles in a predetermined pattern on said housing within the well at angles with respect to the longitudinal and radial directions of the well to hold said bristles in a network extending across substantially the entire cross-sectional area of the well at the location of said bristles, to form a tortuous path for liquid and vapor flowing downwardly therepast, and to cause said bristles to direct liquid which consequently contacts said bristles to migrate along said bristles in the direction thereof most nearly like the net flow direction of the vapor in the well, said bristle supporting means including:

(i) means supporting said bristles for changing said angles thereof with respect to the longitudinal and radial directions of the well to change the radial component of said direction in which said bristles cause the liquid which contacts said bristles to flow and to cause said bristles to direct liquid in contact therewith along said bristles accordingly, such that:

(a) when said bristle supporting means supports said bristles angled radially outwardly in a downward direction toward the wall of the well said bristles will direct the liquid which comes in contact with said bristles outwardly toward the wall of the well, and (b) when said bristle supporting means supports said bristles angled radially inwardly in a downward direction substantially toward the center of the well said bristles will direct the liquid which comes in contact with said bristles inwardly toward the center of the well, (ii) a central core around which said bristles are attached in a predetermined pattern radiating substantially uniformly outwardly around said central core and curved to a position substantially tangent to and touching the wall of the well, and (iii) clamp means for clamping said bristles to said central core.

15. A liquid/vapor separation method for downhole use with a steam thermal recovery process wherein steam is being injected downwardly through a well into a hydrocarbon bearing formation surrounding the well, comprising:

(a) holding a plurality of wire filament bristles, formed of a material wettable by the liquid flowing therepast, within the well at angles with respect to the longitudinal and radial directions of the well in a network extending across substantially the entire cross-sectional area of the well at the location of the bristles, to form a tortuous path for liquid and vapor flowing downwardly therepast, said holding step including the steps of:

(i) supporting bristles substantially all of which have a length greater than the radius of the well, and (ii) clamping the bristles to a central core in a predetermined pattern radiating radially outwardly from the central core substantially uniformly therearound, and such that substantially each bristle is curved to a position substantially tangent to and touching the wall of the well, (b) by means of the bristles, directing liquid which contacts the bristles to migrate along the bristles in the direction thereof most nearly like the net flow direction of the vapor in the well, (c) supporting the bristles for changing the angles thereof with respect to the longitudinal and radial directions of the well to change the radial component of the direction in which the bristles cause the liquid which contacts the bristles to flow to cause the bristles to direct liquid in contact therewith along the bristles accordingly, such that:

(i) when the bristles are angled radially outwardly in a downward direction toward the wall of the well the bristles will direct the liquid which comes in contact with the bristles outwardly toward the wall of the well, and (ii) when the bristles are angled radially inwardly in a downward direction substantially toward the center of the well the bristles will direct the liquid which comes in contact with the bristles inwardly toward the center of the well, (d) centering the bristles in the well, (e) intercepting at least a portion of the steam fluid flowing past the bristles in the well and measuring the liquid/vapor profile thereof, and (f) controlling whether the liquid or vapor phase enters a particular predetermined zone in the well by placing the liquid on the wall of the well when the liquid phase is to enter the zone and removing the liquid phase from the wall when the vapor phase is to enter the zone.

16. A liquid/vapor separator for downhole use with a steam thermal recovery process wherein steam is being injected downwardly through a well into a hydrocarbon bearing formation surrounding the well, comprising:

(a) a plurality of bristles disposed within the well, and (b) bristle supporting means supporting said bristles within the well angled radially outwardly in a downward direction toward the wall of the well and in substantial contact with the wall thereof to hold said bristles in a network extending across substantially the entire cross-sectional area of the well at the location of said bristles, to form a tortuous path for liquid and vapor flowing downwardly therepast, and to cause said bristles to direct liquid which consequently contacts said bristles to migrate along said bristles outwardly toward the wall of the well.

17. A liquid/vapor separator for downhole use with a steam thermal recovery process wherein steam is being injected downwardly through a well into a hydrocarbon bearing formation surrounding the well, comprising:

(a) a plurality of bristles disposed within the well, and (b) bristle supporting means supporting said bristles within the well at angles with respect to the longitudinal and radial directions of the well and in substantial contact with the wall thereof, said bristle supporting means including a central core around which said bristles are attached in a predetermined pattern radiating outwardly therefrom, and clamp means for clamping said bristles to said central core, to hold said bristles in a network extending across substantially the entire cross-sectional area of the well at the location of said bristles, to form a tortuous path for liquid and vapor flowing downwardly therepast, and to cause said bristles to direct liquid which consequently contacts said bristles to migrate along said bristles in the direction thereof most nearly like the net flow direction of the vapor in the well.

18. A liquid/vapor separator for downhole use with a steam thermal recovery process wherein steam is being injected downwardly through a well into a hydrocarbon bearing formation surrounding the well, comprising:

(a) a plurality of bristles disposed within the well, and (b) bristle supporting means supporting said bristles within the well at angles with respect to the longitudinal and radial directions of the well and in substantial contact with the wall thereof, said bristle supporting means including a central core around which said bristles are attached in a predetermined pattern radiating outwardly therefrom, and means supporting said bristles in the well such that substantially each said bristle is curved to a position substantially tangent to and touching the wall of the well, to hold said bristles in a network extending across substantially the entire cross-sectional area of the well at the location of said bristles, to form a tortuous path for liquid and vapor flowing downwardly therepast, and to cause said bristles to direct liquid which consequently contacts said bristles to migrate along said bristles in the direction thereof most nearly like the net flow direction of the vapor in the well.

19. The apparatus of claim 18 wherein substantially all of said bristles each have a length greater than the radius of the well.

20. A liquid/vapor separator for downhole use with a steam thermal recovery process wherein steam is being injected downwardly through a well into a hydrocarbon bearing formation surrounding the well, comprising:

(a) a plurality of bristles disposed within the well, (b) bristle supporting means supporting said bristles within the well at angles with respect to the longitudinal and radial directions of the well and in substantial contact with the wall thereof to hold said bristles in a network extending across substantially the entire cross-sectional area of the well at the location of said bristles, to form a tortuous path for liquid and vapor flowing downwardly therepast, and to cause said bristles to direct liquid which consequently contacts said bristles to migrate along said bristles in the direction thereof most nearly like the net flow direction of the vapor in the well, and (c) said bristle supporting means supporting said bristles for changing said angles thereof with respect to the longitudinal and radial directions of the well to change the radial component of said direction in which said bristles cause the liquid which contacts said bristles to flow to cause said bristles to direct liquid in contact therewith along said bristles in the opposite radial direction.

21. A liquid/vapor separation method for downhole use with a steam thermal recovery process wherein steam is being injected downwardly through a well into a hydrocarbon bearing formation surrounding the well, comprising:

(a) holding a plurality of bristles disposed within the well, and in substantial contact with the wall thereof, angled radially outwardly in a downward direction toward the wall of the well in a network extending across substantially the entire cross-sectional area of the well at the location of the bristles, to form a tortuous path for liquid and vapor flowing downwardly therepast, and (b) by means of the bristles, directing liquid which contacts the bristles to migrate along the bristles outwardly toward the wall of the well.

22. A liquid/vapor separation method for downhole use with a steam thermal recovery process wherein steam is being injected downwardly through a well into a hydrocarbon bearing formation surrounding the well, comprising:

(a) holding a plurality of bristles disposed within the well, and in substantial contact with the wall thereof, by clamping the bristles to a central core in a predetermined pattern radiating outwardly therefrom at angles with respect to the longitudinal and radial directions of the well in a network extending across substantially the entire cross-sectional area of the well at the location of the bristles, to form a tortuous path for liquid and vapor flowing downwardly therepast, and (b) by means of the bristles, directing liquid which contacts the bristles to migrate along the bristles in the direction thereof most nearly like the net flow direction of the vapor in the well.

23. A liquid/vapor separation method for downhole use with a steam thermal recovery process wherein steam is being injected downwardly through a well into a hydrocarbon bearing formation surrounding the well, comprising:

(a) holding a plurality of bristles disposed within the well, and in substantial contact with the wall thereof, by attaching the bristles to a central core in a predetermined pattern radiating outwardly therefrom and supporting the bristles in the well such that substantially each bristle is curved to a position substantially tangent to and touching the wall of the well, the bristles being held at angles with respect to the longitudinal and radial directions of the well in a network extending across substantially the entire cross-sectional area of the well at the location of the bristles, to form a tortuous path for liquid and vapor flowing downwardly therepast, and (b) by means of the bristles, directing liquid which contacts the bristles to migrate along the bristles in the direction thereof most nearly like the net flow direction of the vapor in the well.

24. The method of claim 23 further comprising supporting bristles wherein substantially all of the bristles each have a length greater than the well.

25. A liquid/vapor separation method for downhole use with a steam thermal recovery process wherein steam is being injected downwardly through a well into a hydrocarbon bearing formation surrounding the well, comprising:

(a) holding a plurality of bristles disposed within the well, and in substantial contact with the wall thereof, at angles with respect to the longitudinal and radial directions of the well in a network extending across substantially the entire cross-sectional area of the well at the location of the bristles, to form a tortuous path for liquid and vapor flowing downwardly therepast, (b) by means of the bristles, directing liquid which contacts the bristles to migrate along the bristles in the direction thereof most nearly like the net flow direction of the vapor in the well, and (c) supporting the bristles for changing the angles thereof with respect to the longitudinal and radial directions of the well to change the radial component of the direction in which the bristles cause the liquid which contacts the bristles to flow to cause the bristles to direct liquid in contact therewith along the bristles in the opposite radial direction.

26. A liquid/vapor separation method for downhole use with a steam thermal recovery process wherein steam is being injected downwardly through a well into a hydrocarbon bearing formation surrounding the well, comprising:

(a) holding a plurality of bristles disposed within the well, and in substantial contact with the wall thereof, at angles with respect to the longitudinal and radial directions of the well in a network extending across substantially the entire cross-sectional area of the well at the location of the bristles, to form a tortuous path for liquid and vapor flowing downwardly therepast, (b) by means of the bristles, directing liquid which contacts the bristles to migrate along the bristles in the direction thereof most nearly like the net flow direction of the vapor in the well, and (c) intercepting at least a portion of the steam fluid flowing past the bristles in the well and measuring the liquid/vapor profile thereof.

27. The method of claim 26 further comprising measuring substantially vapor flow only.

28. The method of claim 26 further comprising measuring substantially liquid flow only.

29. A liquid/vapor separation method for downhole use with a steam thermal recovery process wherein steam is being injected downwardly through a well into a hydocarbon bearing formation surrounding the well, comprising:

(a) holding a plurality of bristles disposed within the well, and in substantial contact with the wall thereof, at angles with respect to the longitudinal and radial directions of the well in a network extending across substantially the entire cross-sectional area of the well at the location of the bristles, to form a tortuous path for liquid and vapor flowing downwardly therepast,
(b) by means of the bristles, directing liquid which contacts the bristles to migrate along the bristles in the direction thereof most nearly like the net flow direction of the vapor in the well, and
(c) controlling whether the liquid or vapor phase enters a particular predetermined zone in the well by placing the liquid on the wall of the well when the liquid phase is to enter the zone and removing the liquid phase from the wall when the vapor phase is to enter the zone.

* * * * *